(12) United States Patent
O'Rourke

(10) Patent No.: US 7,225,408 B2
(45) Date of Patent: May 29, 2007

(54) SYSTEM AND USER INTERFACE FOR COMMUNICATING AND PROCESSING PATIENT RECORD INFORMATION

(75) Inventor: Kevin O'Rourke, Downingtown, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 557 days.

(21) Appl. No.: 09/939,886

(22) Filed: Aug. 27, 2001

(65) Prior Publication Data

US 2002/0158911 A1    Oct. 31, 2002

Related U.S. Application Data

(60) Provisional application No. 60/287,644, filed on Apr. 30, 2001, provisional application No. 60/287,273, filed on Apr. 27, 2001.

(51) Int. Cl.
*G06F 3/00* (2006.01)

(52) U.S. Cl. ............... 715/743; 715/733; 715/744; 715/748; 715/864

(58) Field of Classification Search ........ 345/705–715, 345/810, 846, 847, 853–855; 705/1–3; 709/203; 715/705–715, 810, 846, 853–855, 715/847; 707/3, 4, 10, 100, 102, 104; 128/903, 128/920; 600/300
See application file for complete search history.

(56) References Cited

U.S. PATENT DOCUMENTS

| | | | | |
|---|---|---|---|---|
| 5,267,155 A | * | 11/1993 | Buchanan et al. | 715/540 |
| 5,327,341 A | * | 7/1994 | Whalen et al. | 705/3 |
| 5,400,794 A | | 3/1995 | Gorman | 128/696 |
| 5,687,734 A | | 11/1997 | Dempsey et al. | 128/696 |
| 5,772,585 A | * | 6/1998 | Lavin et al. | 600/300 |
| 5,812,865 A | | 9/1998 | Theimer et al. | 395/800 |
| 5,823,948 A | * | 10/1998 | Ross et al. | 600/300 |
| 5,832,450 A | * | 11/1998 | Myers et al. | 705/3 |
| 5,845,255 A | * | 12/1998 | Mayaud | 705/3 |
| 5,857,967 A | | 1/1999 | Frid et al. | 600/301 |
| 5,867,662 A | | 2/1999 | Riggs | 395/200.58 |

(Continued)

OTHER PUBLICATIONS

Screen Dumps of Microsoft Internet Explorer version 5.0 (pp. 1-3, 1999).*

(Continued)

*Primary Examiner*—Sy D. Luu
(74) *Attorney, Agent, or Firm*—Alexander J. Burke

(57) ABSTRACT

A system facilitates the secure access, transfer and update of patient record information and the creation and navigation of image menus supporting the location and access of desired patient record data by a user. A system provides a user interface for use by a portable processing device for accessing and navigating patient record information. The system receives user identification information for use in authorizing user operation of the portable processing device and initiates display of an image including a plurality of links to a corresponding plurality of individual patients. The system also initiates display of a patient record content index image including a plurality of links to a corresponding plurality of items of patient record information in response to user selection of a link to one of the plurality of individual patients. The system further initiates display of an image including information comprising a portion of a patient record in response to user selection of a link to one of the plurality of items of patient record information.

22 Claims, 17 Drawing Sheets

U.S. PATENT DOCUMENTS

| | | | |
|---|---|---|---|
| 5,880,724 A * | 3/1999 | Bertram et al. | 715/780 |
| 5,903,889 A * | 5/1999 | de la Huerga et al. | 707/3 |
| 5,924,074 A * | 7/1999 | Evans | 705/3 |
| 5,928,329 A | 7/1999 | Clark et al. | 709/227 |
| 5,950,168 A * | 9/1999 | Simborg et al. | 705/3 |
| 5,961,608 A | 10/1999 | Onosaka et al. | 709/249 |
| 6,006,274 A | 12/1999 | Hawkins et al. | 709/248 |
| 6,009,247 A | 12/1999 | Canora et al. | 395/309 |
| 6,074,345 A | 6/2000 | van Oostrom et al. | 600/300 |
| 6,088,595 A | 7/2000 | Ciccone et al. | 455/463 |
| 6,111,570 A | 8/2000 | Sugikawa et al. | 345/329 |
| 6,128,661 A | 10/2000 | Flanagin et al. | 709/227 |
| 6,134,504 A | 10/2000 | Douglas et al. | 702/31 |
| 6,150,951 A | 11/2000 | Olejniczak | 340/825.03 |
| 6,208,344 B1 * | 3/2001 | Holzman et al. | 715/846 |
| 6,211,797 B1 | 4/2001 | Kimura | 340/825.72 |
| 6,213,942 B1 | 4/2001 | Flach et al. | 600/300 |
| 6,263,330 B1 * | 7/2001 | Bessette | 707/4 |
| 6,272,468 B1 * | 8/2001 | Melrose | 705/2 |
| 6,476,833 B1 * | 11/2002 | Moshfeghi | 715/854 |
| 6,587,829 B1 * | 7/2003 | Camarda et al. | 705/3 |
| 6,606,659 B1 * | 8/2003 | Hegli et al. | 709/225 |
| 6,610,010 B2 * | 8/2003 | Sjoqvist | 600/300 |
| 6,678,397 B1 * | 1/2004 | Ohmori et al. | 382/128 |
| 6,775,670 B2 | 8/2004 | Bessette | |
| 2002/0013815 A1 * | 1/2002 | Obradovich et al. | 709/204 |
| 2002/0019751 A1 * | 2/2002 | Rothschild et al. | 705/3 |
| 2004/0203352 A1 * | 10/2004 | Hall et al. | 455/41.1 |

OTHER PUBLICATIONS www.memaster.ca MediLink A SmartCard-Assisted Wearable Data Acquisition and Communication system for Emergency and Mobile Medicine, no date.
www.biomed.ntua.gr/emergency112, no date.
U.S. Appl. No. 09/939,899, filed Aug. 27, 2001, Kevin O'Rourke.
U.S. Appl. No. 09/939,965, filed Aug. 27, 2001, Kevin O'Rourke.

* cited by examiner

| HEME SURVEY | BURCH, THOMAS |
|---|---|
| | 01 JUL 99 | 15 SEP 95 06:46 |
| WBC | 22.0 | 8.0 |
| RBC | | 3.90 |
| HGB | | 13.0 |
| HCT | | 34.0 |
| MCV(MCV) | | 89.0 |
| MCHC(MCHC) | | 33.0 |
| RBC DIST WIDTH ( | | 14.1 |
| PLATELET (PLTT) | | |
| REL WBC DIFF (%) | | |

14Sep95  08 Sep 95

941 — (pointing to 22.0)
943 — (pointing to 8.0)

FIG. 15

| REF RANGES | BURCH, THOMAS |
|---|---|

951 — WBC 3.5-8.5 K/UL
RBC 3.80-5.00 M/UL
HGB 11.8-15.4 G/DL
HCT 35.0-45.0 ML/DL
MCV(MCV) FL/RBC
MCHC(MCHC) 33.0-37.0 G/DL RBC
RBC DIST WIDTH (RDW) 12.0-15.0
PLATELET (PLTT) 170-380 K/UL
%TOT.NEUT (TNEUT) % WBC
%SEGS (SEGS) % WBC
%BANDS (BAND) % WBC
%LYMPHS (LYMP) % WBC

FIG. 16

ROW HEADERS
LOCK WHEN
SCROLLING
LEFT/RIGHT
970

CLOUMN HEADERS
LOCK WHEN
SCROLLING
UP/DOWN
973

| HEME SURVEY | BURCH, THOMAS | ▷ |
|---|---|---|
| | 01 JUL 99 | 15 SEP 95 |
| | | 06:46 |
| WBC | 22.0 | 8.0 |
| RBC | | 3.90 |
| HGB | | 13.0 |
| HCT | | 34.0 |
| MCV(MCV) | | 89.0 |
| MCHC(MCHC) | | 33.0 |
| RBC DIST WIDTH ( | | 14.1 |
| PLATELET (PLTT) | | |
| REL WBC DIFF (%) | | |
| | 14 SEP 95 | 08 SEP 95 |

FIG. 18

ROUNDSTRACKER BLOOM, VALERIE ▷

BED: 327  AGE: 55          SEX: F DOB:01

ADM: 14 MAR 01             MR: 123456789

DIAGNOSES:
▽ -- SELECT DIAGNOSIS --
▽ -- SELECT DIAGNOSIS --
▽ -- SELECT DIAGNOSIS --
▽ -- SELECT DIAGNOSIS --
[                                          ]

CODE STATUS:
▽ -- SELECT STATUS --
[                                          ]

FIG. 20B

SYSTEM AND USER INTERFACE FOR COMMUNICATING AND PROCESSING PATIENT RECORD INFORMATION

This application is concurrently filed together with commonly owned related application Ser. No. 09/939,899 filed 27 Aug. 2001, and Ser. No. 09/939,965 filed 27 Aug. 2001

This is a non-provisional application of provisional applications Ser. No. 60/287,273 by K. O'Rourke filed Apr. 27, 2001 and Ser. No. 60/287,644 by K. O'Rourke filed Apr. 30, 2001.

FIELD OF THE INVENTION

This invention concerns a system and user interface for use by a portable processing device or other device for communicating medical record information of a patient.

BACKGROUND OF THE INVENTION

The use of the traditional patient chart document by physicians in periodic hospital rounds and for other functions is hampered by many limitations. The chart needs to be located, reviewed and commandeered by a physician preventing others from using it and the chart is readily subject to being misplaced or mistreated. Other limitations include the absence of an efficient patient chart indexing mechanism and the associated difficulty of locating particular information (especially where the chart is bulky and covers lengthy, periodic, or complex treatment regimes). In addition, the fact that there is a single copy of the chart means it typically is kept near the patient limiting chart access for review and analysis by a physician at a later time and a different location. Similarly, a single copy of the chart also makes it difficult to keep the chart up-to-date with details of the latest treatment orders and test results.

The advent of computerized patient records enabling access to current information from many locations has addressed some of these issues. However, electronic patient record processing systems are also constrained by limitations. Specifically, computer access terminals are often not at the point of care. This requires a physician to print a report or carry the original paper chart in order to obtain a portable record. In contrast, a portable patient record processing device permits a physician to access and search current patient record information at the point of care using tools provided by the computerized patient record system. Ideally, the portable device, such as a palmtop computer, has a display large enough to easily view a patient record yet small enough to facilitate portability. However, available portable systems for processing patient record information are limited in their capabilities for securely accessing, transferring and updating patient record information and in their capabilities for creating and navigating image menus supporting the location and access of desired patient record data by a user. A system according to invention principles addresses these problems and derivative problems

SUMMARY OF INVENTION

A system facilitates the secure access, transfer and update of patient record information and the creation and navigation of image menus supporting the location and access of desired patient record data by a user. A system for use by a first portable processing device for transferring medical record information of a patient between portable processing devices involves selecting information to be transferred in response to user command. The system also involves establishing a communication link with a second portable processing device and communicating patient identification information and the selected information on the established communication link in response to user selection of a displayed icon.

In a feature of the invention, the system supports user navigation through a plurality of display images to enable selection of the information to be transferred, in response to user command.

In a further feature of the invention, the system involves configuring the method of transferring patient record information between portable processing devices by pre-selecting data elements comprising the patient identification information.

BRIEF DESCRIPTION OF THE DRAWING

FIGS. 9-20 show image menus supporting user access and navigation of patient medical record information for display on a portable processing device, according to invention principles.

DETAILED DESCRIPTION OF THE DRAWING

Figure 1:
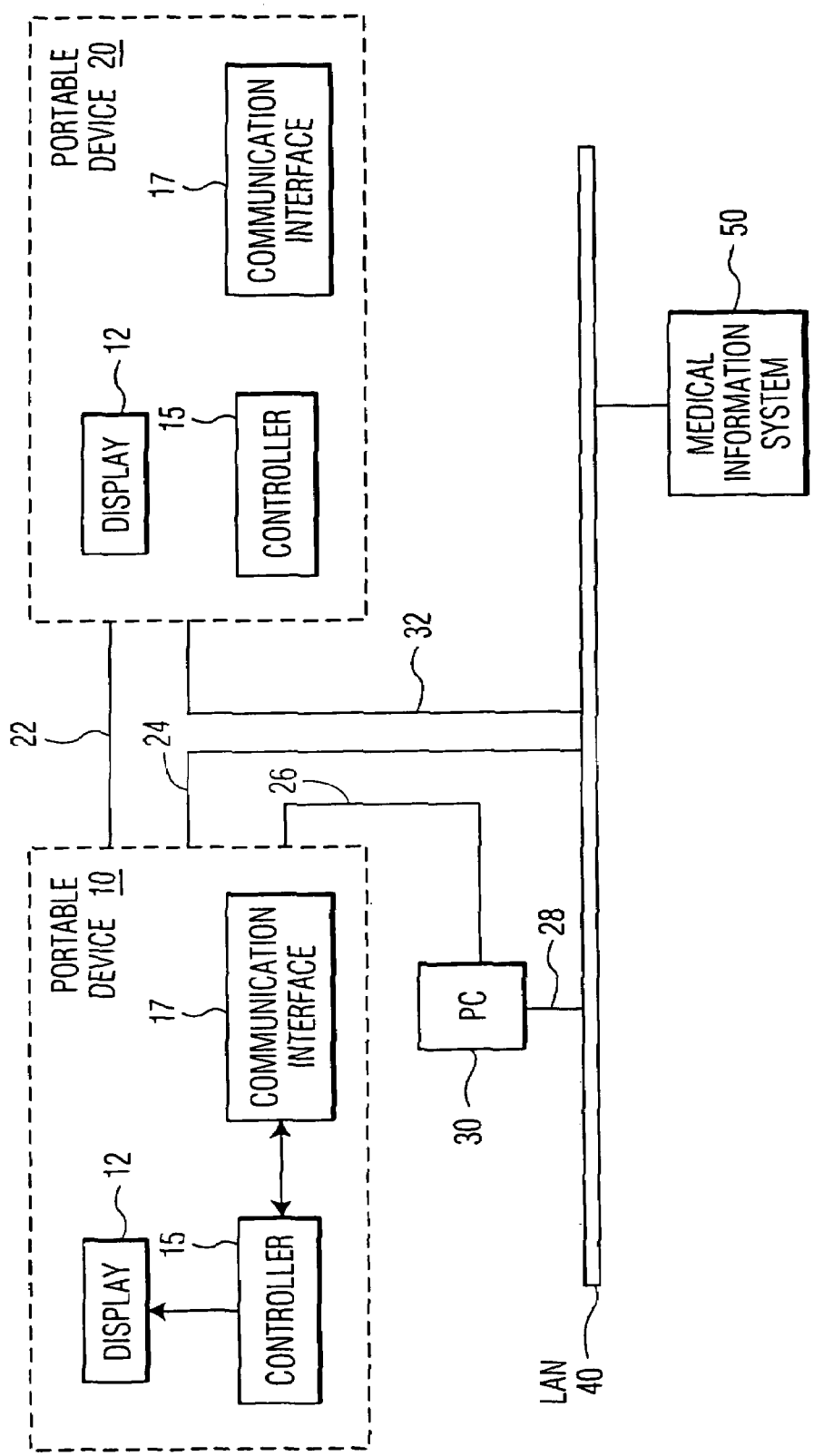
FIG. 1 shows a network supporting the transfer of patient medical record information between portable processing devices, according to invention principles.

FIG. 1 shows a network system supporting the transfer of patient medical record information between portable devices as well as the secure access, and update of medical record information in a record repository. Patient information acquired following user data entry via a portable processing device is uploaded to the patient record repository and may be printed or passed to another portable processing device using an infrared serial connection or another connection.

Further, individual portable processing devices support the creation and navigation of image menus enabling the location and access of desired medical record data by a user. A user of a portable processing device is able to download a complete medical record or a portion of a record for either, a specific patient, or a user-specified list of patients from a patient record repository using a variety of communication links. Such communication links include, for example, serial connections to PC or server serial ports using serial cradles or infra-red transceiver connections, Ethernet connections to PC or server Ethernet ports using Ethernet cradles or infra-red transceiver connections and other WAN (Wide Area Network) and LAN (Local Area Network) and wireless connections.

Patient medical record and other information from a patient record repository is downloaded to a portable processing device for storage by the device. The downloaded information is specially formatted for the portable device display and is viewed using a browser optimized for navigating healthcare information on the display. The downloaded patient record information is accessible by a user of the portable processing device without requiring a persistent connection to the patient record repository. Further, a user is able to advantageously initiate another application on the device whilst concurrently viewing a patient record. For this purpose patient information is transparently passed to the initiated application and upon completion of the initiated application control returns to the original application managing the displayed patient record.

The network architecture of FIG. 1 is exemplary only. The portable processing devices may operate in a variety of network environments involving one or more hierarchically arranged LANs or WANs including Ethernet-compatible LANs (used to connect different hospital departments, for example) and multiple Medical Interface Buses (MIBs) for corresponding multiple patients. In addition, a portable processing device is able to access the Internet via a firewall and other intra-nets (not shown) using a dial-up telephone connection, ADSL, cable modem or other types of connection. Individual portable processing devices are Internet Protocol (IP) compatible but may also employ other protocols supporting communication connectivity among the networked devices.

The network system of FIG. 1 supports the transfer of patient medical record information between portable devices 10 and 20 as well as the secure access and update of medical record information in the record repository of information system 50. Portable devices 10 and 20 each comprise a controller 15 for processing data and commands received via communication interface 17 as well as via data entry from attached data entry devices including a keyboard and mouse or other cursor controls (not shown to preserve drawing clarity). Controller 15 initiates display of menus and acquired information on display 12 and bi-directionally communicates with medical information system 50 and other portable processing devices and Internet and other Intra-net connections via communication interface 17. Portable processing devices 10 and 20, using controllers 15 and interfaces 17, directly bi-directionally communicate with each other via an infra-red serial port connection 22 and also communicate with each other and information system 50 and the Internet and other intra-net systems, for example, using other communication links. Such other communication links include a serial connection 26 to PC 30 and from PC 30 via Ethernet connection 28 to LAN 40 and system 50 (or the Internet and other external connections via a firewall, for example). Alternatively device 10 may directly communicate via Ethernet connection 24 with LAN 40 and system 50. Similarly, portable device 20 may directly communicate via Ethernet connection 32 with LAN 40 and system 50. Further, the serial and Ethernet connections may also involve wireless connections including infra-red or other connections.

Figure 2:
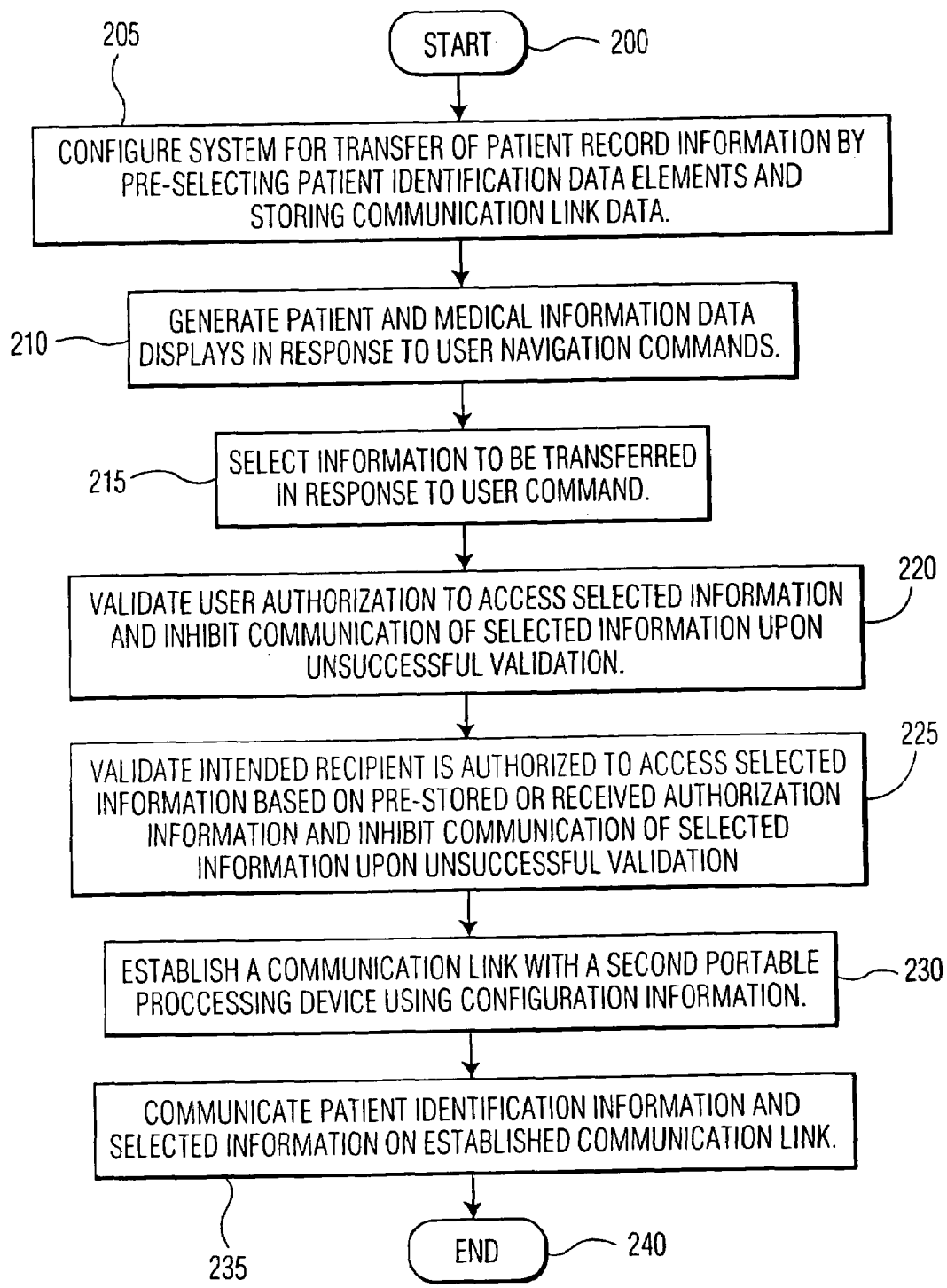
FIG. 2 shows a flowchart of a process for transferring patient medical record information between portable processing devices, according to invention principles.

FIG. 2 shows a flowchart of a process used by controller 15 of portable processing device 10 for transferring patient medical record information to portable processing device 20. In step 205, following the start at step 200, controller 15 configures portable processing device 10 for patient record transfer. A user operating portable processing device 10 (including controller 15) stores communication link associated settings and pre-selects data elements comprising patient identification information. Thereby a user configures processing device 10 by pre-selecting patient identification data elements to be communicated to support patient record transfer. A user may select data elements such as username, password, patient identifier, patient gender identifier, patient birth date and calling application identification (supporting return of control to a calling application upon completion of communication) to be communicated upon a patient record transfer, for example. In similar fashion, a user configures processing device 10 with communication settings such as data rate, a protocol identifier, sender identifier code, error handling code identifier and data format identifier. Further, a user also configures processing device 10 to sequentially initiate communication on multiple different links in establishing a viable communication link with portable processing device 20 or another device. For this purpose, a user selects a predetermined hierarchy of communication links to be tried in establishing communication as well as a predetermined time-out window within which a return communication acknowledgement is expected and the number of times which each link may be tried until an attempt failure is declared.

In step 210, controller 15 generates a sequence of patient and medical information menus in response to user navigation commands. The sequence of menus supports user navigation and enables user selection of information elements to be transferred to portable processing device 20 in step 215. User selected information elements to be transferred may include, for example, medical information associated with a group of patients, and medical information associated with a specific patient. Other user selected information elements to be transferred may include, laboratory test results for a specific patient, a medical report associated with a group of patients and medical information associated with a specific healthcare provider and an associated group of patients. In step 220, controller 15 validates that the user of processing device 10 is authorized to access the information selected for transfer (e.g., via password verification) and inhibits communication of those selected information elements for which the user is denied access. Processing device 10 (in conjunction with controller 15) inhibits acquisition and storing by device 20 of selected information elements for which the user is denied access in order to prevent their communication to processing device 20.

In step 225, controller 15 of processing device 10 validates that the user of processing device 20, the intended recipient of the information, is authorized to access the information selected for transfer. Controller 15 does this based on pre-stored authorization information (e.g. a password) or on information communicated to processing device 10 from device 20 identifying the device 20 user as an authorized recipient of the selected information elements. Upon unsuccessful validation, controller 15 inhibits transfer of the selected information. Upon successful validation, controller 15 in step 230 establishes communication with portable processing device 20 via interface 17 using the communication settings previously selected in step 205. Controller 15 in step 235 communicates the selected information elements together with the associated patient identification information elements (previously identified in step 205 to accompany a data transfer) on the established communication link. If an Infra-Red communication link is established, step 235 involves a user pointing an IR port of device 10 at the receiving device 20. Thereby, patient information selected on portable processing device 10 is transferred to a user of portable processing device 20.

Figure 19:
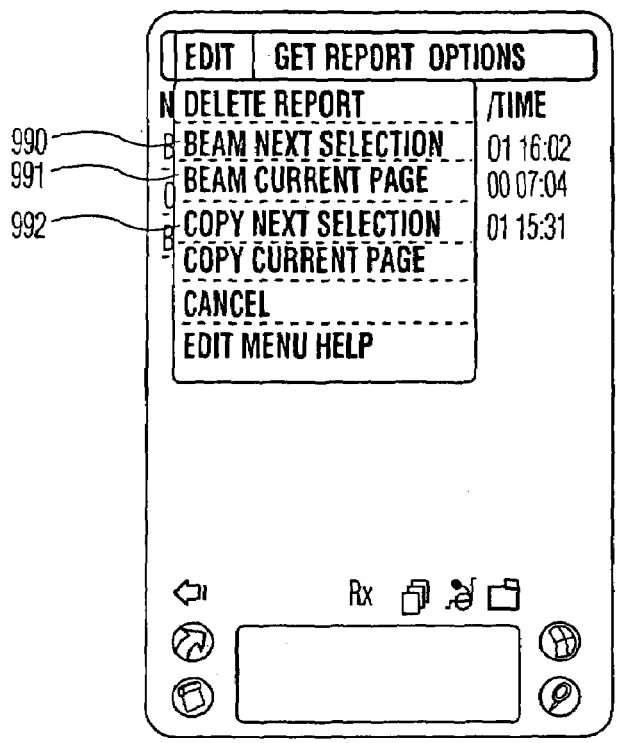

A user may transfer an entire list of patients, details of an individual patient, or a set of results for a patient, for transfer in the previously described manner. In order to transfer (or "beam") a set of information, a user selects a "Beam Next Selection", menu item 990, in the user interface display image of FIG. 19, for example and selects the information to send. In order to send a list of patients, a user may select a report from a report list menu such as census report 900 of FIG. 9. In order to send a patient record, a user may select a patient (e.g., Valerie Bloom item 908) from a patient list shown in FIG. 10. In order to send a set of results, a user may select a set (e.g., allergies test results item 911 for Valerie Bloom) from a Valerie Bloom's chart index list shown in FIG. 11. Alternatively, a current page of information may be selected for transfer. For this purpose a user may select "Beam Current Page" item 991 of FIG. 19 and controller 15 initiates transfer of the current patient details or information set that is currently being displayed. A similar technique is used to copy information to an internal clipboard of device 10. In this case, a user selects a "Copy" function, e.g., item 992 instead. Information subsequently selected is copied to the clipboard where it is available for pasting into other device 10 applications or for printing. The process of FIG. 2 terminates at step 240.

Figure 3:
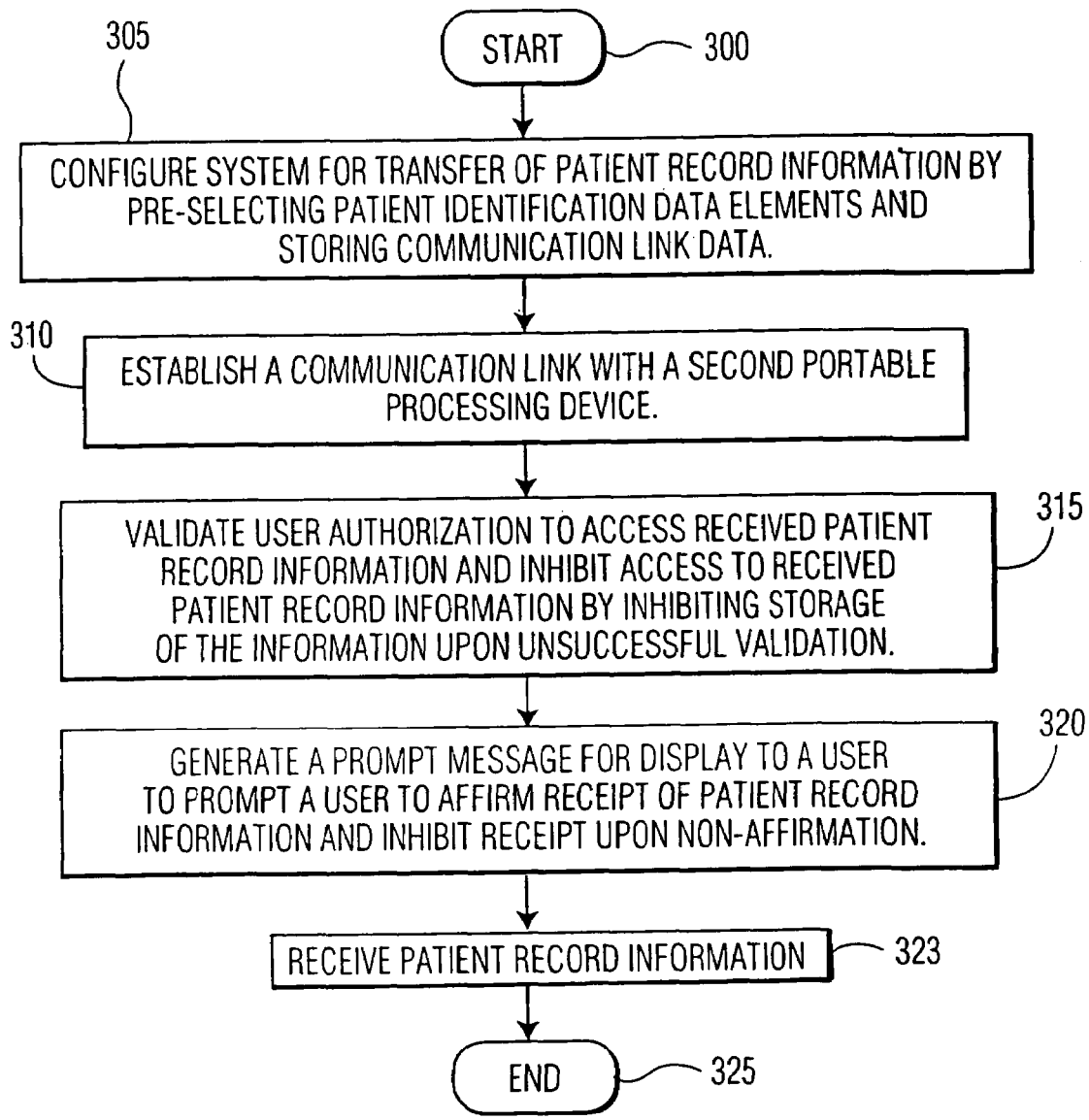
FIG. 3 shows a flowchart of a process for use by a portable processing device for receiving patient medical record information transferred from another portable processing device, according to invention principles.

FIG. 3 shows a flowchart of a process for use by a portable processing device for receiving patient medical record information transferred from another portable processing device. In step 305, following the start at step 300, controller 15 configures portable processing device 20 for patient record transfer in the manner employed for processing device 10 in step 205 of FIG. 2. In response to receiving a communication initiation message from processing device 10, controller 15 of processing device 20 establishes communication with portable processing device 10 via interface 17 in step 310 of FIG. 3 using the communication settings previously selected in step 305. In step 315, controller 15 of receiving processing device 20 initiates generation and display of a message prompt to a user. The displayed message prompt solicits a user to enter a password in order to receive patient medical record information transferred from processing device 10.

Upon unsuccessful validation of the entered password, controller 15 of receiving processing device 20 inhibits receipt of the transferred information. Alternatively controller 15 in another embodiment may inhibit storage of transferred information. Upon validation of the entered password, controller 15, in step 320, initiates generation and display of a further message prompt to a user requesting the user to affirm that receipt of the medical record information from processing device 10 is accepted. If a user does not affirm that receipt is accepted controller 15 inhibits receipt and storage of transferred patient medical record information. In response to password validation and an affirmation of receipt, the patient medical record information is received in step 323 and stored on receiving processing device 20 to be available for display. The process of FIG. 3 terminates at step 325.

Figure 4:
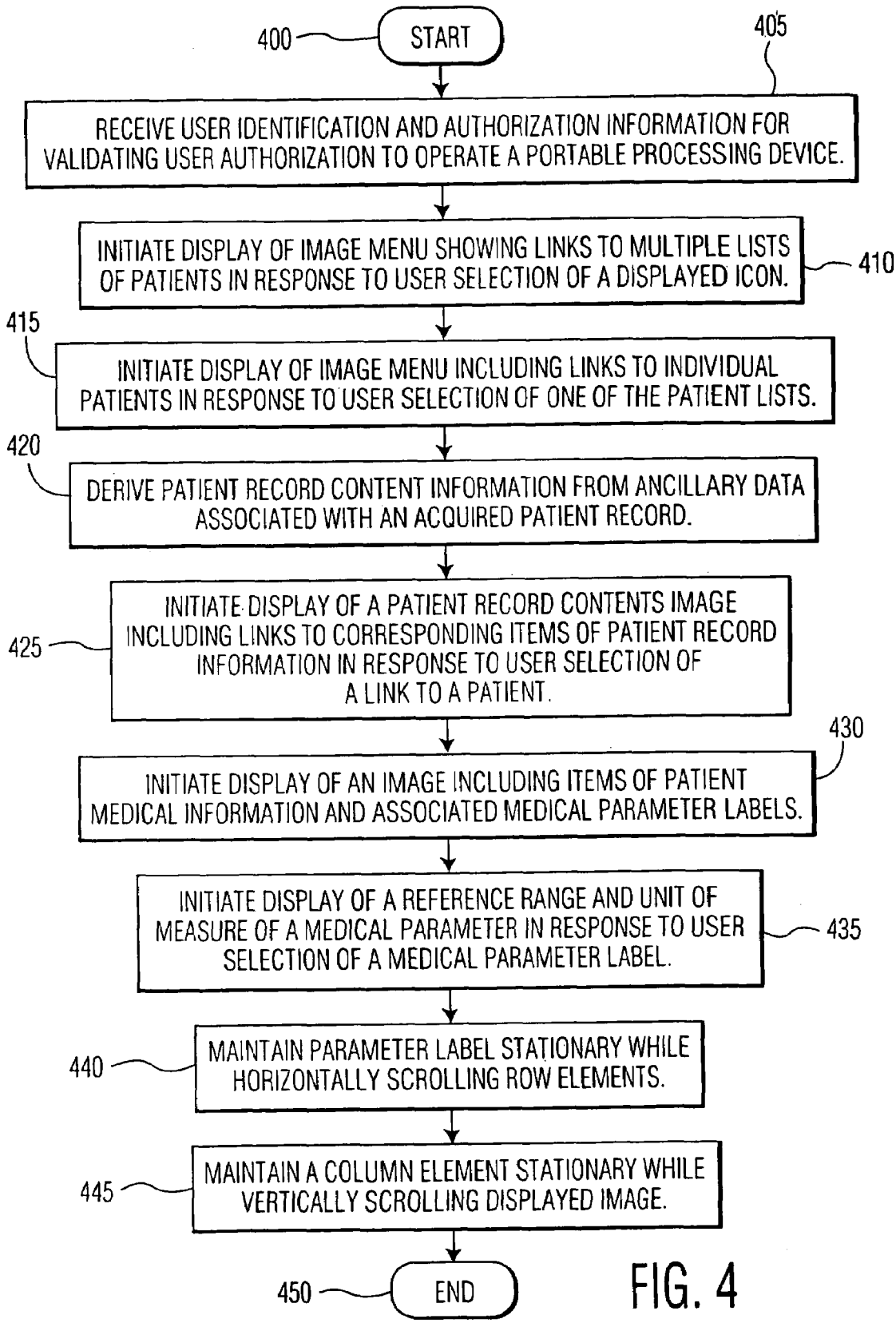
FIG. 4 shows a flowchart of a process for use by a portable processing device for providing menus supporting user navigation and access to desired patient medical record information, according to invention principles.
Figures 9, 10:
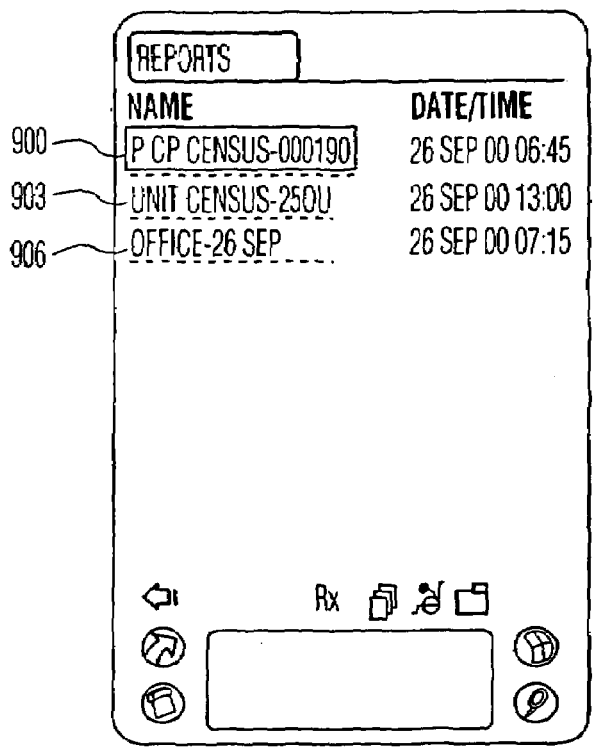
Figures 11, 12:
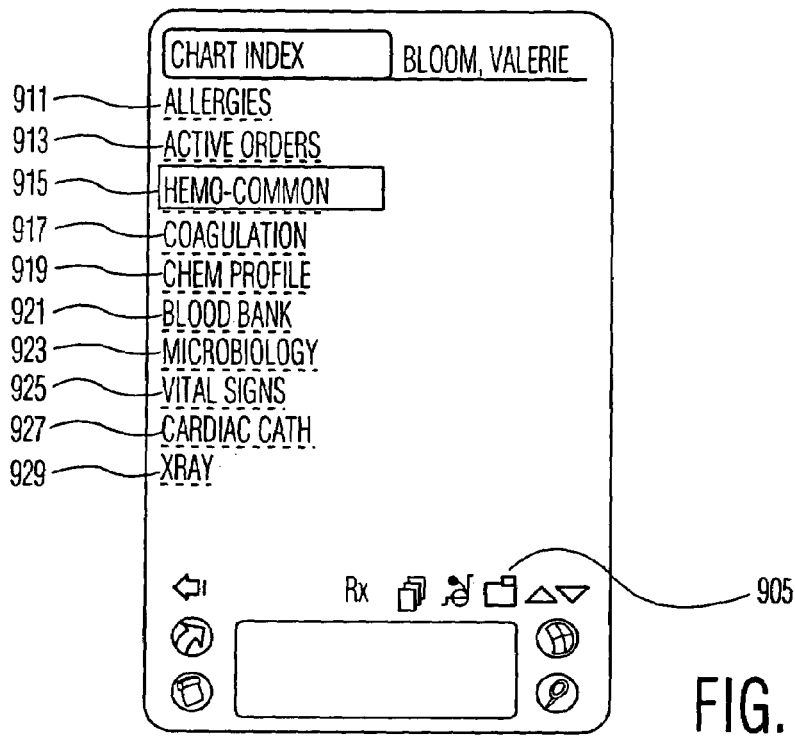

FIG. 4 shows a flowchart of a process for use by a portable processing device for providing menus supporting user navigation and access to desired patient medical record information. In order to access a patient medical report, a user initiates operation on device 10 of an application for accessing a patient record and is prompted to enter a password. The password is required to continue operation of the patient record access application and is also required to access the desired electronic patient medical record itself. In step 405, following the start at step 400, controller 15 verifies a user entered password is valid in response to user selection of a logon icon. In response to successful validation controller 15 in step 410 initiates display of links to multiple lists of patients as exemplified by links 900, 903 and 906 in the menu of FIG. 9. The link items 900, 903 and 906 comprise hyperlinks to report names representing different lists of patients. In step 415 controller 15 initiates display of a menu exemplified in FIG. 10 including links (e.g., links 908 and 909 of FIG. 10) to patient record information of individual patients in response to user selection of patient list link 900 (FIG. 9). Further in response to user selection of link to an individual patient (e.g., Valerie Bloom link 908) an index (corresponding to a patient chart index) to the patient record for this patient is displayed as shown in FIG. 11. The patient record index is advantageously accessible by a user of processing device 10 by selecting an icon button (e.g. icon 905 of FIG. 11) on a browser toolbar presented in the different menus displayed on device 10. This facilitates rapid access to the key elements of a patient record from any menu.

An advantage of the disclosed system is the ease of locating information in a patient record. This is facilitated by the dynamic generation by controller 15 in step 420 of a patient record content index. It is a hyperlinked content index to each of the major sections of a patient chart such as Chemistry, Hematology, Vital Signs etc. as exemplified in elements 911-929 of FIG. 11. The patient record content index is created dynamically by a remote application running on a server as the patient record information is generated and communicated to processing device 10. As the server application collates individual sections of a patient record for communication to processing device 10, it also creates individual URL links to corresponding record sections for use in a patient record content index. Specifically, as a new section of patient record data is retrieved from a record repository, a name of that section (e.g. Chemistry) is identified and stored in a memory buffer as an HTML hyperlink tag pointing to the report section it references The server application derives content index information from collated patient record information by parsing the patient record information or by parsing ancillary data associated with the patient record information. This is done in order to identify distinct patient record information sections for listing in a content index page as URL links to patient record sections. The ancillary data comprises, for example, header data of the patient record information, descriptive data in a data field of acquired patient record information, identification data in a data field of acquired patient record information, and text data derived by parsing content of acquired patient record information. Upon completion of collation of patient record for an individual patient for communication to processing device 10, the server application creates an additional record section for incorporation in the patient record comprising the patient record content index incorporating the created links for the corresponding patient record sections. In another embodiment, the patient record content index is created within processing device 10 in response to receiving a patient medical record by parsing received patient medical record data to identify section headings for listing in a contents index page.

Figure 13:
Figure 14:

In step 425 controller 15 initiates display of a patient record index for a patient (Valerie Bloom) as shown in FIG. 11 in response to user selection of link 908 (FIG. 10). Further, in step 430 controller 15 initiates display of a desired section (e.g., a Hemo-Common—hematology section detailing common blood test results) of the patient record for the patient (Valerie Bloom) in response to user selection of Hemo-Common link 915 (as shown in FIG. 11). In this manner a user is able to advantageously navigate directly to desired patient record sections by selecting a hyperlinked index item associated with the desired patient record section (e.g., items 911-929 of FIG. 11). The desired Hemo-Common patient record section comprising patient laboratory test results selected in step 430 is shown in FIG. 12. The displayed results include labels, e.g., item 930 wbc (white blood count) identifying the test together with test values obtained on different measurement days. In addition, patient record text section names occurring in a patient record, such as CT Scans (ITEM 933), Nuclear Medicine (item 935) and Special procedures (item 937) of FIG. 13 may also link to portions of a patient record. Selecting CT Scans 933 results in display of text section 939 of FIG. 14, for example.

Another exemplary section listed on a patient record index is a link to a Heme-survey menu which may also be selected and displayed in step 430, for example, in response to user selection of a Heme-survey link in a patient record index. The Heme-survey menu of FIG. 15 similarly shows labels, e.g., wbc (white blood count) identifying a test together with test values (e.g., items 941 and 943). In step 435, in response to user selection of a displayed label (e.g., wbc) in the Heme-survey menu (or the menu of FIG. 12) a reference range for the wbc test is displayed in FIG. 16 (item 951) indicating the range of normal values for a given type of result together with the associated unit of measure. For example, hemoglobin (hgb) show a normal (or reference) range of 11.8 to 15.4 grams per deciliter. The use of a separate menu to indicate a reference range and unit of measure for a parameter or test result, in response to selection of a parameter label hyperlink, advantageously preserves limited display space on a portable processing device display screen.

In a further navigation feature illustrated in FIG. 18, row and column leading items such as items 970 and 973 are automatically locked as a user scrolls. For this purpose controller 15 in step 440 maintains item 970 stationary whilst a user horizontally scrolls the screen image, thereby advantageously enabling a user to associate a result value with a parameter (e.g. wbc 970) as the user horizontally scrolls through values of the parameter. Similarly, controller 15 in step 445 maintains item 973 stationary whilst a user vertically scrolls the screen image, thereby advantageously enabling a user to associate parameter values with a test date 973 as a user vertically scrolls through different parameters and associated values. The process of FIG. 4 terminates at step 450.

Figure 5:
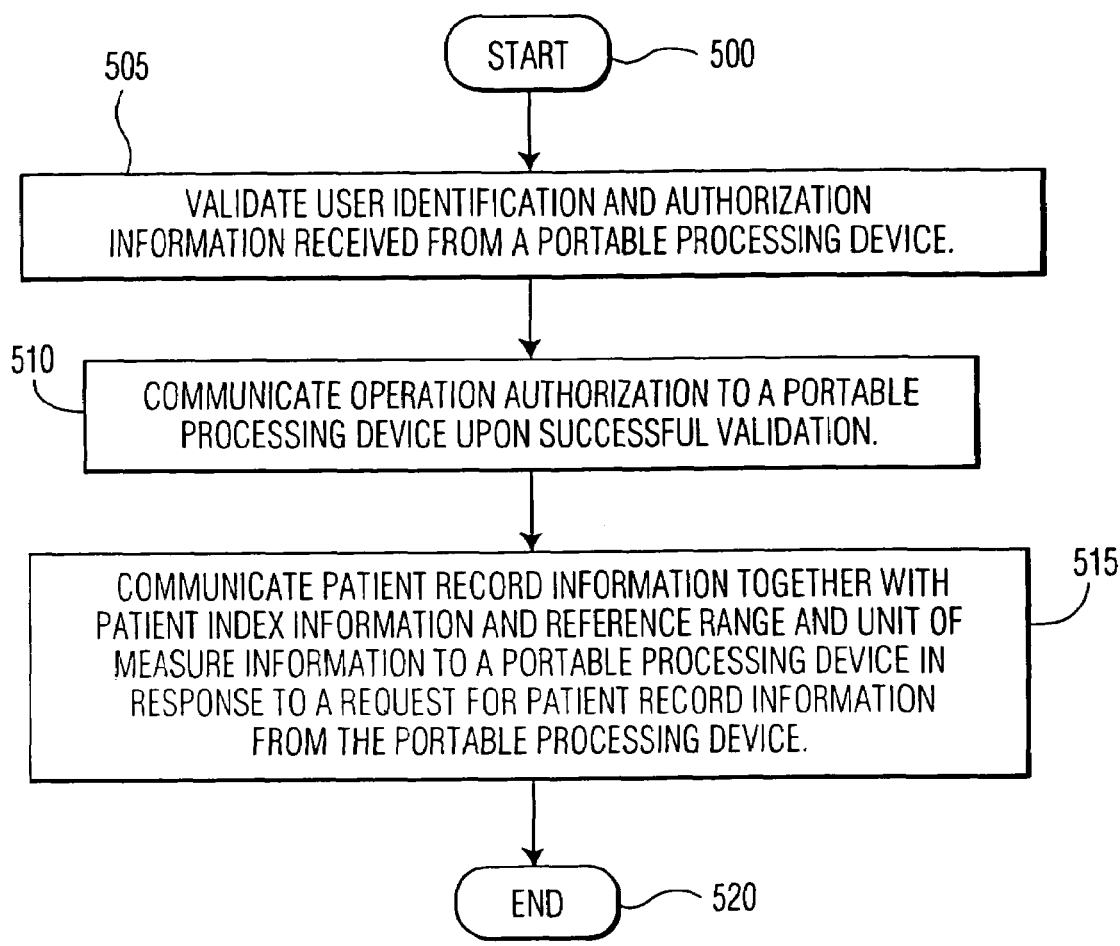
FIG. 5 shows a flowchart of a process for supporting remote operation of a plurality of portable processing devices used for accessing and navigating patient record information, according to invention principles.

FIG. 5 shows a flowchart of a process used by a remote system (e.g. system 50 of FIG. 1) for supporting remote operation of a plurality of portable processing devices used for accessing and navigating patient record information. In step 505, following the start at step 500, user identification information received from portable processing device 10 is validated. Upon successful validation, an authorization message enabling a user to operate portable processing device 10 (or another device) is communicated in step 510 to device 10 (or the other device). Also, in response to a request for patient record information from a validated user, patient record information is communicated to portable processing device 10 in step 515. The patient record information communicated to device 10 includes a server generated patient record content index and other information menus including reference range and unit of measure information associated with a medical parameter and parameter label as previously described in connection with FIG. 4. Alternatively, the patient record content index may be dynamically generated in device 10 as previously described in connection with FIG. 4. The process of FIG. 5 terminates at step 520.

Figure 6:
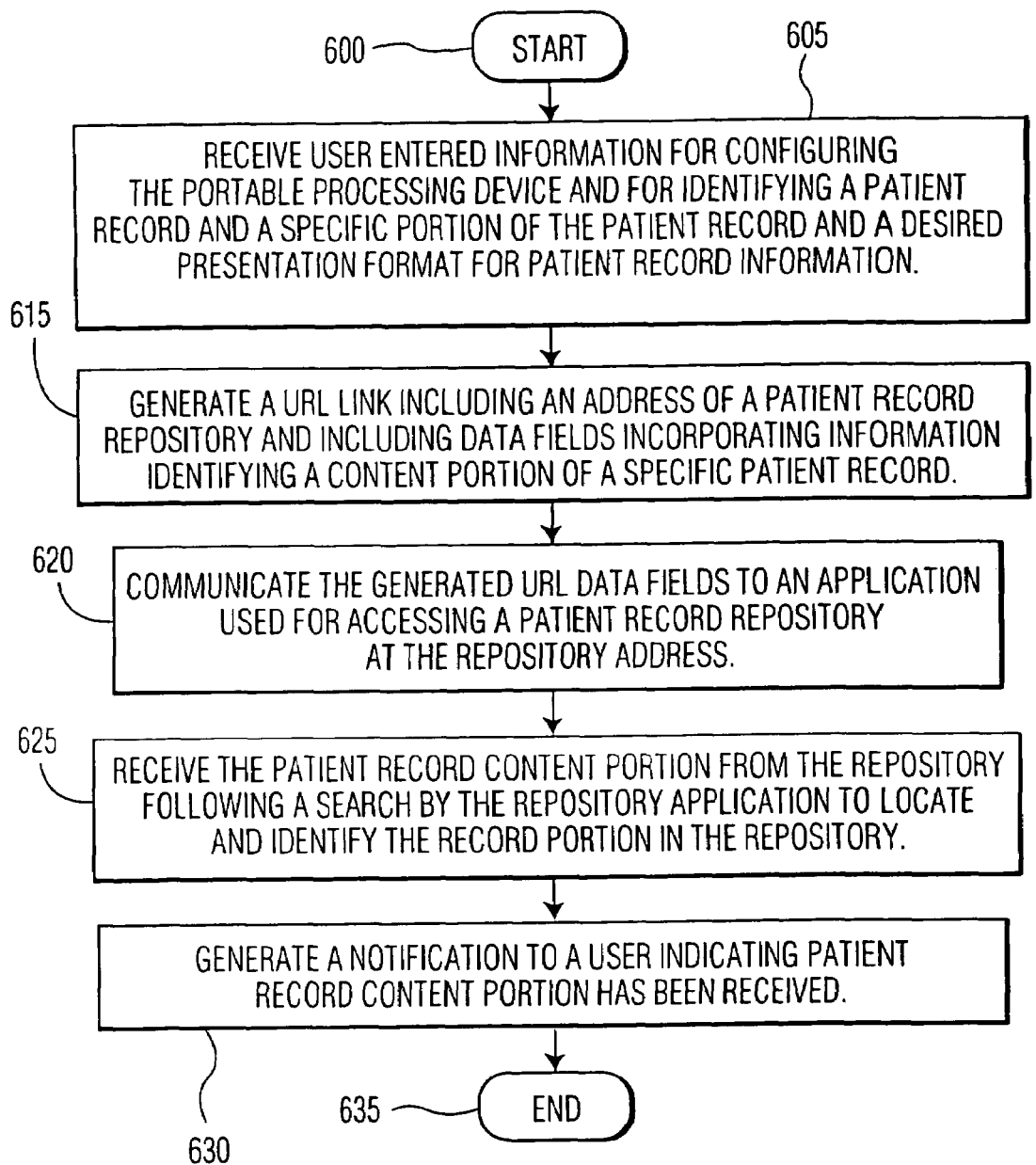
FIG. 6 shows a flowchart of a process for use by a portable processing device for securely accessing patient medical record information, according to invention principles.

FIG. 6 shows a flowchart of a process for use by a portable processing device for securely accessing patient medical record information. In step 605, following the start at step 600, controller 15 of portable processing device 10 receives configuration information to support download of medical record information from a patient record repository maintained by system 50 (FIG. 1). The configuration information represents preferences determining the type and format of medical record information to be received. The preferences are set by a user via an operating system application of processing device 10. The configuration information comprises, for example, (a) a URL of a patient record repository, (b) a proxy server address, (c) codes to access a patient record repository such as user logon information, (d) lists of patients to be accessed, (e) content type of a patient record (f) format of a patient record (g) a list of appointments and (h) particular sections of a patient record to be acquired (e.g., orders, allergies, results by department etc.). Further, a list of patients may comprise a physician's attending patient census list, a group census list, a hospital nurse station patient census list or a hospital service census list. Alternatively, a patient list may comprise information identifying one or more patients by a record number. The configuration information may also determine a sort order and format (e.g., date across against date down) of patient record information to be sent as well as whether reference range and unit of measure information is to be sent. Additional configuration preferences may determine, (i) whether all or a portion of a text report is to be sent, (ii) whether a portion of a report to be sent should commence at the beginning of the report or at the end, (iii) whether result comments are to be sent and (iv) whether a list of patients is to appear as a checklist to enable a physician to individually check off each patient. Controller 15 retains the configuration settings until they are amended by a user.

In step 615, controller 15 generates a URL including an address of the system 50 record repository and data fields in query format including information derived from the configuration information. Specifically, the data fields include information about the user and information identifying a specific content portion of a particular patient medical record to be acquired. In step 620, the generated URL is communicated to an application at the repository address used by system 50 in accessing its patient record repository. For this purpose, portable processing device 10, establishes communication with the system 50 application via a PC or server serial ports using a serial cradle or infra-red transceiver connection or via an Ethernet connection to PC or server Ethernet ports using an Ethernet cradle or infra-red transceiver connection or other WAN (Wide Area Network), LAN (Local Area Network) or wireless connection.

In step 625, the system 50 application searches the record repository to locate and identify the requested medical record portion in response to the URL query data and creates HTML (Hypertext Markup Language) pages from the located patient medical record information. The created HTML pages are formatted for the portable processing device 10 display in the manner determined by the URL query data fields in accordance with the configuration information entered in step 605. The resultant patient record portion, in HTML page format, is transmitted from system 50 to processing device 10. Processing device 10 receives the HTML page medical record content portion and processes it for storage. In similar fashion, medical record information for multiple different patients may be requested in a single URL query and acquired by device 10. In step 630, controller 15 generates a message for display notifying a user that the requested patient record content portion has been received and is available for access and display. The process of FIG. 6 terminates at step 635.

Figure 7:
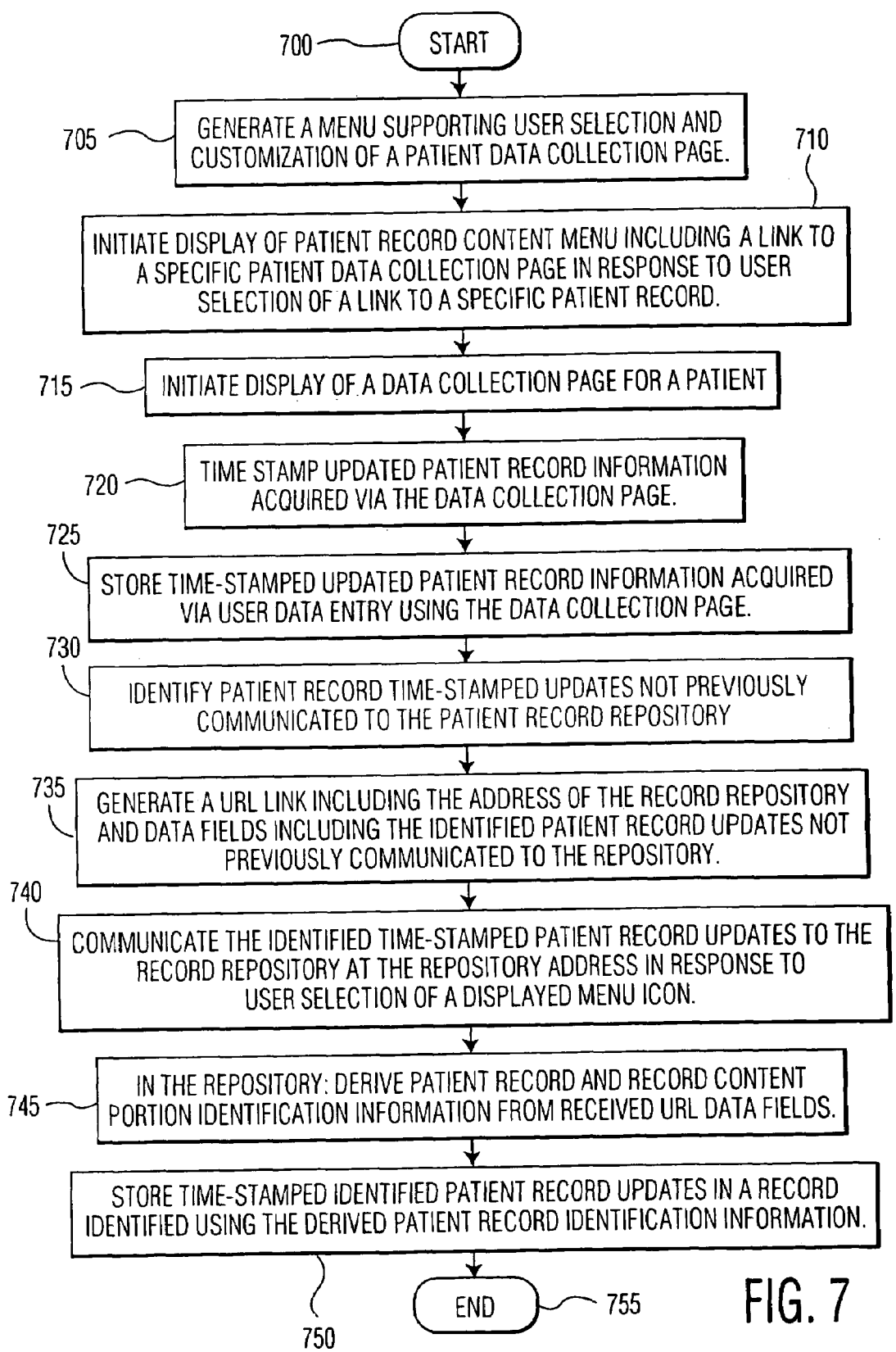
FIG. 7 shows a flowchart of a process for use by a portable processing device for securely updating patient medical record information, according to invention principles.

FIG. 7 shows a flowchart of a process for use by a portable processing device for securely updating patient medical record information. A physician, upon seeing a patient, commonly needs to update the medical record of the patient to indicate that tests have been ordered, medications have been prescribed, a diagnosis has been made, or to include other notes, for example. Traditionally, this has been handwritten into a paper chart. However, by enabling a portable processing device to record and send this information while a physician is currently seeing a patient significantly contributes to easing the task burden of the physician. In order to record and update information, an HTML display page formatted for a portable processing device is advantageously provided for capturing individual patient details. Further, individual users of a portable processing device may have their own data capture page tailored to their own requirements. A customized data capture page is stored within a portable processing device and is accessed using a hyperlink in the associated patient record content index (e.g., a hyperlink (not shown) to the collection page is added to the patient record content index of FIG. 11). When selected, the user's data collection page, called the RoundsTracker, is displayed as exemplified in FIG. 20B. The data collection page shows data previously recorded for a patient and enables a physician to make additions or corrections to this data prior to storage of the page as a record associated with a current patient.

In step 705, following the start at step 700, controller 15 of portable processing device 10 initiates display of a menu supporting user selection and customization of a patient data collection page. A user may customize a data collection page to include data fields for receiving particular items of patient information, for example. In response to user selection of a link to a patient record (e.g. selection of link 908 (FIG. 10), controller 15 in step 710 initiates display of a patient record content menu as exemplified by FIG. 11 modified to include a hyperlink (not shown) to a data collection page. In response to user selection of the link to the data collection page, controller 15 in step 715 initiates display of the data collection page (e.g., an HTML page) as exemplified in FIG. 20B. Controller 15 time stamps updated patient record information acquired via the data collection page in step 720 and stores the time stamped information in step 725.

Controller 15 identifies those time stamped patient record updates and amendments that have not been previously communicated to the patient record repository of system 50 (FIG. 1) in step 730. Further, in step 735, controller 15 generates a URL including an address of the system 50 record repository and data fields in query format including the identified patient record updates not previously communicated to the repository. Using the generated URL, controller 15 in step 740 communicates the identified time stamped patient record updates to the system 50 repository at the repository address in response to user initiation of communication via a displayed menu icon. In step 745, at the system 50 patient record repository, the patient record and record content portion to be updated are identified using the identification information derived from the received URL data fields. If an error was detected by system 50 in receiving the updated information then the information is retransmitted from the portable processing device in response to an error notification from system 50. The time stamped patient record updates and amendments are stored in the identified record content portion in step 750 and the process of FIG. 7 terminates at step 755.

The updated patient record information collected via one or more data collection pages may be sent to update a record repository as in FIG. 7 or may be Emailed to another remote location or may be printed. For this purpose controller 15 initiates display of a menu including selectable icons allowing user selection of Print, Email or record repository update options. If the print option is selected a portable processing device uses an, infrared port to send the updated data collection information in printer compatible format to an infrared capable printer in response to a user command. Specifically the portable processing device sends to the printer those pages that have not been previously printed. Alternatively, another communication link, e.g., a serial port link, may be used to do this. The stored information in the portable processing device is time stamped to indicate the time of printing. If a problem in printing is detected the data collection pages are resent to the printer.

If the Email option is selected a portable processing device Emails the updated data collection pages, time stamped to indicate they were sent, to an Email address or a fax destination as required, in response to user command. For this purpose a user enters an email destination address via the displayed menu options. In similar fashion to the record update and print functions, various communication mechanisms may be used for the Email function including, Ethernet, serial link, and wireless mechanisms as previously described. In addition, a problem detected in Emailing the information results in the data collection pages being resent.

Figure 8A:
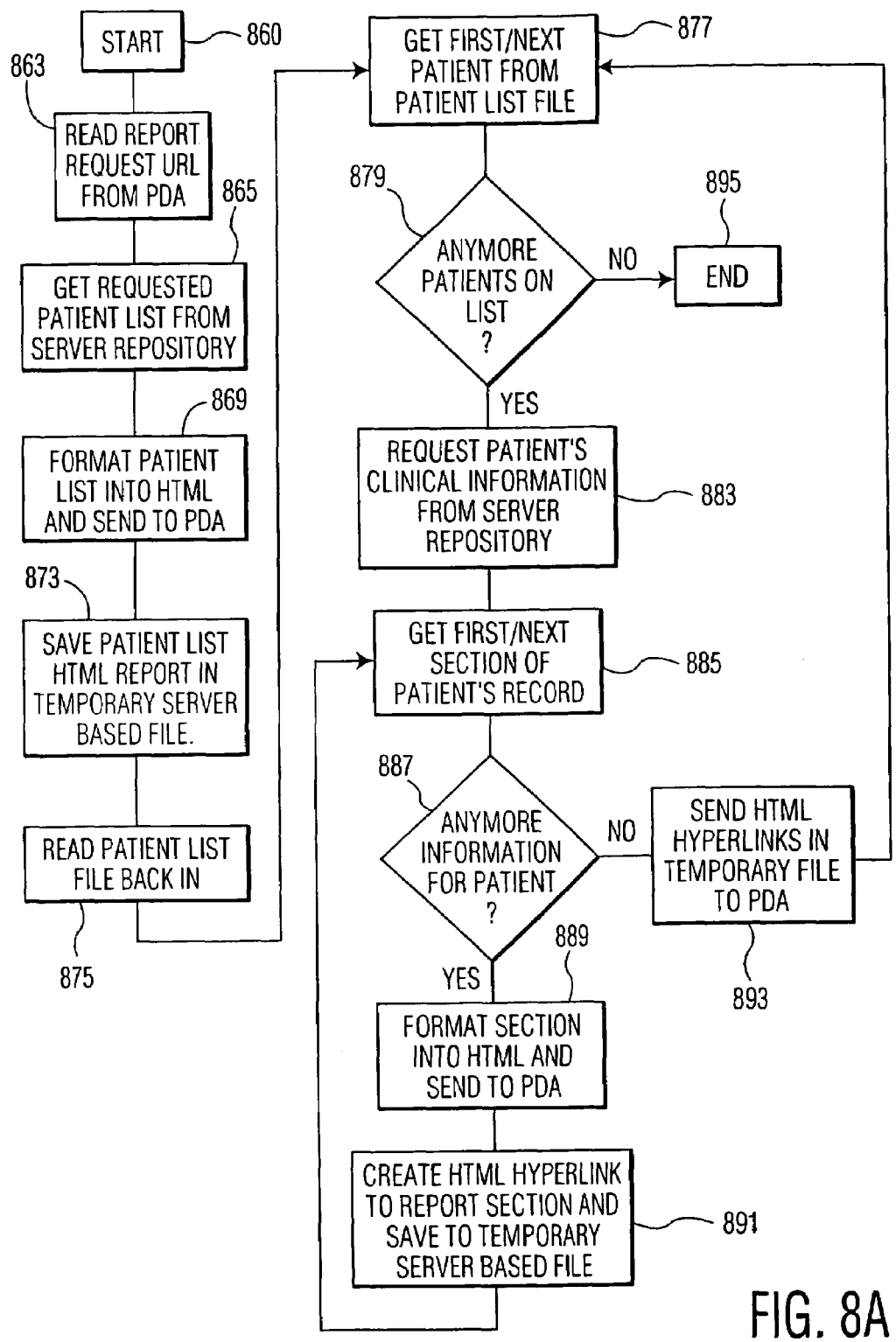
FIG. 8A shows a flowchart of a process used in generating a patient list menu and a content index information menu for provision to a plurality of remote portable processing devices, according to invention principles.

FIG. 8A shows a flowchart of a process used by a record repository server application, for example, in generating a patient list menu and a content index information menu for provision to a plurality of remote portable processing devices. In step 863, following the start at step 860, a server application derives a request for a list of patients from URL data fields received from a portable processing device. The application retrieves the requested list of patients from the repository in step 865, converts and formats the list to be HTML compatible and communicates the HTML list to the portable processing device in step 869. The application also saves the HTML patient list in temporary storage in step 873 and reads the list entries in step 875. The application successively performs the procedure between steps 877 and 895 for each patient on the list in order. Specifically, a patient from the list is identified in step 877 and if information for the last patient on the list has already been processed, the process terminates at step 895. If there are any more patients on the list to be processed, as determined in step 879, clinical information is requested for the identified patient from the record repository in step 883.

The application successively performs the procedure between steps 885 and 893 for each section of a patient record of each patient on the requested list of patients. Specifically, a section of a patient record is identified in step 885 and there are any more record sections to be processed, as determined in step 887, the identified patient record section is formatted to be HTML compatible and communicated to the portable processing device in step 889. In addition, an HTML hyperlink is created to the patient record section and saved in a temporary storage file in step 891. Once steps 889 and 891 are performed for each identified patient record section, the hyperlinks stored in the temporary storage file, comprising a patient record content index, are communicated as a page to the portable processing device. Thereby, patient record information and an associated patient record content index is communicated by the application to the portable processing device for each patient in the requested patient list derived from the received URL data fields.

Figure 8B:
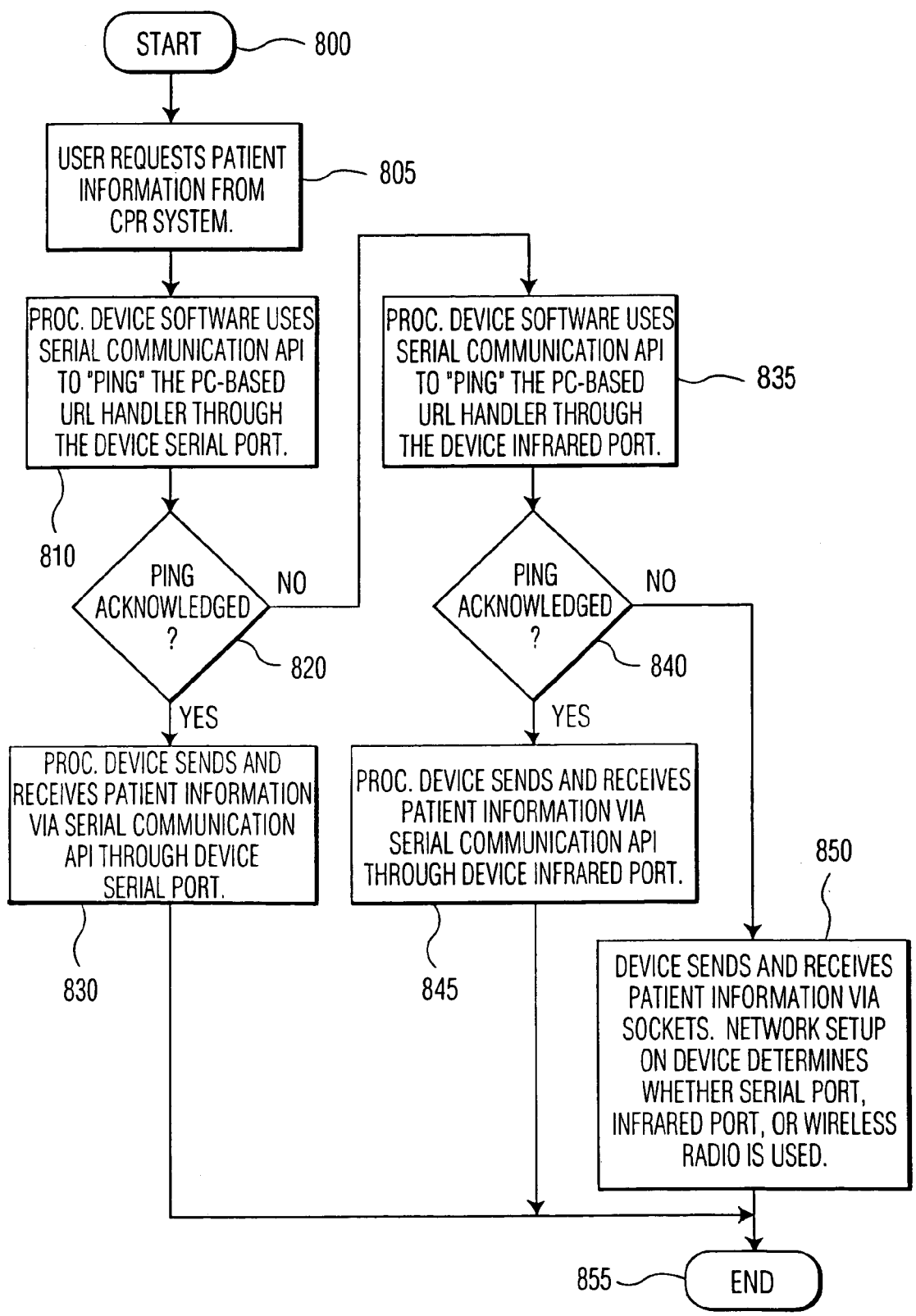
FIG. 8B shows a flowchart of a process for establishing a communication link with another device by sequentially initiating communication on individual communication links until an acknowledgement is received within a predetermined time-out window, according to invention principles.

FIG. 8B shows a flowchart of a process for automatically establishing a communication link with another device by sequentially initiating communication on different communication links until an acknowledgement is received within a predetermined time-out window. Controller 15, in conjunction with interface 17 of portable processing device 10, establishes communication with another device using a serial connection (using a portable device cradle), an Ethernet connection, a wireless connection or an infra-red connection. Following the start at step 800, and upon a request by a user in step 805 to acquire information from the system 50 record repository, a user connects processing device 10 to an access point such as a cradle, infrared transceiver or wireless LAN. In step 810, controller 15 (FIG. 1) uses a serial communication API (Application Programming Interface) to interrogate ("ping") a URL handler in PC 30 (FIG. 1) through a serial port of portable processing device 10. If the processing device 10 is connected to a serial cradle, the URL Handler in PC 30 acknowledges device 10 in step 820 (FIG. 8B) and a bi-directional communication link is established. A URL generated by device 10 is then sent via the serial connection in step 830 in the manner previously described.

If the interrogation of step 810 fails to receive an acknowledgement within one second as determined in step 820, controller 15 (FIG. 1) in step 835 uses the serial communication API (Application Programming Interface) to interrogate ("ping") a URL handler through the processing device 10 infra-red port. If the interrogation via the infra-red port is acknowledged within one second as determined in step 840, device 10 in step 845 (FIG. 8B) bi-directionally communicates patient information with another device via the serial communication API infra-red port.

If controller 15 of processing device 10 in step 840 does not receive an acknowledgement in one second via the infra-red port, it assumes a direct network connection (i.e., not through host PC 30) is to be used. In this case, controller 15 in step 850 sends a generated URL using network socket support provided in the processing device 10 operating system. The network connection setup of processing device 10 is configured to use a serial port (for an Ethernet cradle), an infrared port (for an Ethernet IR transceiver), or a wireless card (for wireless radio connections). If communication by any of the described methods is unsuccessful, the process is repeated once. If no communication link is successfully established after the process repetition, a communication failure indicative message is generated and displayed to a user. The process of FIG. 8B terminates at step 855.

A connection can be made over an intranet or the Internet using any of the methods described above. Internet connections employ encryption and SSL (Secure Socket Layer) protocol to pass healthcare information. For the serial and infra-red connection communication via PC 30, PC-based browser software is used to provide encryption. For the direct network connections, encryption is provided by resident software within processing device 10. An advantage of the iterative communication connection system of FIG. 8B is that the user does not have to pre-configure processing device 10 settings for any particular communication method. Thereby, for example, in the course of a day a user may employ a cradle, infrared, or a network connection without re-configuring device 10.

Figures 17A, 17B:
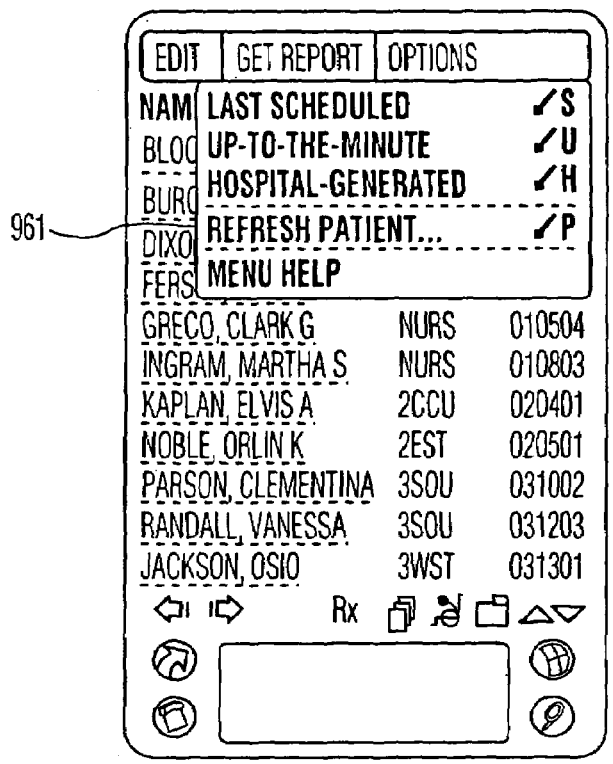

In order to update information from a patient, a user selects a menu refresh command (as exemplified by item 961 of FIG. 17A) and selects the particular patient from a patient list (as exemplified by FIG. 17B). The patient list may be a current census or appointment list or a list of the last 50 patients the user has reviewed which is automatically maintained by processing device 10. A patient list may be presented by device 10 as a checklist allowing a user to check off patients as they are seen. In this case, the state of the checkbox is maintained even if the patient data is refreshed from system 50. Once a patient is selected, device 10 generates a URL to retrieve the specified patient data using an identification number for the particular patient. The URL is sent to the patient record repository of system 50 system. System 50 queries its databases for the information requested for the patient and sorts and formats it as requested. Specifically, system 50 creates HTML pages from the patient information formatted for a palm-sized display, and transmits the data back to device 10 in the manner previously described in connection with FIG. 8A and other figures. Processing device 10 stores then refreshes the information on that patient in the report.

Figure 20A:
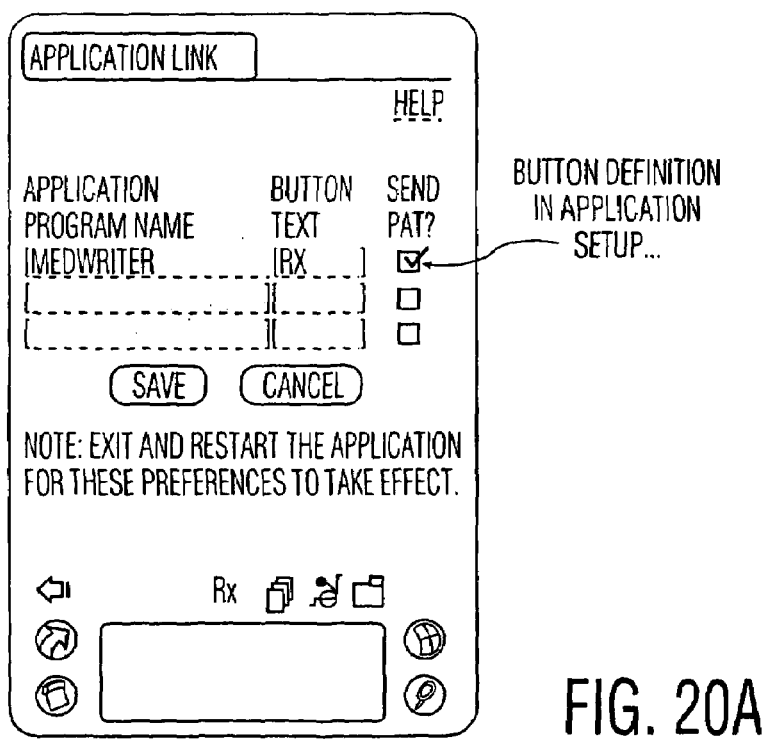

In the course of reviewing patient information, a user may need to consult medical literature or use another application executable on device 10. Such an application may need information about a patient. For example, a prescription writer may need to know patient age, sex, weight, name and a patient identification number. In order to initiate another application on device 10, a user creates a button (e.g., Rx) on an application toolbar and assigns it a name (e.g., Medwriter) using a menu as shown in FIG. 20A. The user also specifies whether patient information is to be passed to the application when it is initiated (exemplified by the ticked check box of FIG. 20A). Upon completion of the set-up, a button (Rx) appears in the toolbar for initiating the specified application and passing it the following patient information in XML format:

<patient id="patient number">
<name>patient name</name>
<birthdate>MM/DD/YYYY</birthdate>
<sex>patient sex</sex>
</patient>

Applications that are called in this way are specially coded to accept the patient information being passed and automatically start their application with the referenced patient queued for processing. In addition to the specified patient information, a username and password are also passed in order to advantageously enable both applications to use the same password.

<user id="username" ps="password"></user>

The name of the calling application (e.g., ClinSumm) is also passed so that the called program can return control when finished.

<calling_program>ClinSumm program name</calling_program>

The architectures and processes presented in FIGS. 1-8 and the user interface menus of FIGS. 9-20 are not exclusive. Other architectures, processes and user interface menus may also be derived in accordance with the principles of the invention to accomplish the same objectives. Further, the inventive principles may be advantageously employed in any clinical health care information management system for facilitating distribution of patient and other information to multiple different locations.

What is claimed is:

1. A method for transferring medical record information of a patient between portable processing devices, comprising the steps of:
   on a first portable processing device,
      selecting information to be transferred in response to user command;
      establishing a bidirectional communication link with a second portable processing device;
      validating identification data of a medical information recipient associated with said second portable device to determine said recipient is authorized to access said selected information; and
      communicating patient identification information and said selected information on said established communication link in response to user selection of a displayed icon.

2. A method according to claim 1, wherein
said established communication link with said second portable processing device includes a wireless link and
said step of selecting information to be transferred comprises selecting at least one of, (a) medical information associated with a plurality of patients, (b) medical information associated with a specific patient, (c) laboratory test results for a specific patient, (d) a medical report associated with a plurality of patients and (e) medical information associated with a specific healthcare provider and an associated group of patients.

3. A method according to claim 2, wherein
said step of selecting information to be transferred includes the step of supporting user navigation, in response to user command, through a plurality of display images to enable selection of said information to be transferred.

4. A method according to claim 1, including the step of configuring said method of transferring patient record information between portable processing devices by pre-selecting data elements comprising said patient identification information.

5. A method according to claim 4, wherein
said data elements comprising said patient identification information include at least two of (a) username, (b) password, (c) patient identifier, (d) patient gender identifier, (e) patient birth date and (f) calling application identification supporting return of control to said calling application upon completion of communication on an established communication link.

6. A method according to claim 1, including the steps of validating user authorization to access said selected information, and
   inhibiting communication of said selected information on said established communication link in response to unsuccessful validation of user authorization to access said selected information.

7. A method according to claim 1, wherein
said bidirectional communication link between said first and second portable processing devices is direct without intervening devices and including the step of
   inhibiting communication of said selected information on said established communication link in response to unsuccessful validation of authorization of said medical information recipient to access said communicated selected information.

8. A method according to claim 7, wherein
said identification data comprises authorization information received by said first portable processing.

9. A method according to claim 1, including the step of storing a plurality of communication settings associated with a plurality of corresponding communication links;
   sequentially initiating communication on individual communication links, one at a time, using associated corresponding communication settings until an acknowledgement is received within a predetermined time-out window indicating a communication link with a second portable processing device is established.

10. A method according to claim 9, wherein
said plurality of communication links comprise at least two (a) connection via a PC compatible serial port, (b) connection via an infra-red link to a PC compatible serial port, (c) connection via an Ethernet compatible network (d) connection via an infra-red link to an Ethernet compatible network and (e) a wireless network connection.

11. A method according to claim 9, wherein
said step of sequentially initiating communication is performed automatically upon detection of a lost connection to support seamless operation of said portable processing device.

12. A method according to claim 9, wherein
said established communication link with said second portable processing device includes a wireless link and
said communication settings comprise a set of communication settings applicable to a corresponding individual communication link.

13. A method according to claim 12, wherein
said set of communication settings include at least two of (a) data rate, (b) protocol identifier, (c) sender identifier code, (d) error handling code identifier and (e) data format identifier.

14. A method according to claim 9, wherein said initiating communication step comprises
   initiating communication on said plurality of communication links one at a time in a predetermined sequential order.

15. A method according to claim 9, including the step of communicating at least two of (a) username, (b) password, (c) patient identifier, (d) patient gender identifier, (e) patient birth date and (f) calling application identification supporting return of control to said calling application upon completion of communication on an established communication link.

16. A method according to claim 9, including the step of repeating said initiating communication step for a predetermined number of times until a connection is established or a communication failure is declared.

17. A method for receiving medical record information communicated to a first receiving portable processing device from a second portable processing device, comprising the steps of:
- on a first receiving portable processing device,
  - validating user authorization to access medical information of a particular patient;
  - establishing a bidirectional communication link with a second portable processing device;
  - validating identification data of a medical information recipient associated with first portable device to determine said recipient is authorized to access medical information of said particular patient;
  - inhibiting access to said medical information in response to unsuccessful validation of said identification data and recipient authorization, said inhibiting access being performed by at least one of,
    - (a) inhibiting receiving said medical information and associated patient identification information on said established communication link, and
    - (b) inhibiting storing said medical information and associated patient identification information received on said established communication link.

18. A method according to claim 17, including the step of initiating generation of a message to prompt a recipient to affirm receipt of said medical information is desired, and
inhibiting receipt of said medical information in response to a non-affirmation.

19. A method according to claim 17, wherein
said established communication link with said second portable processing device includes a wireless link and
said validation of user authorization comprises password validation.

20. A method according to claim 17, including the step of
configuring said method of transferring patient record information between portable processing devices by pre-selecting data elements comprising said patient identification information.

21. A method according to claim 20, wherein
said data elements comprising said patient identification information include at least two of (a) username, (b) password, (c) patient identifier, (d) patient gender identifier, (e) patient birth date and (f) calling application identification supporting return of control to said calling application upon completion of communication on an established communication link.

22. A system for transferring medical record information of a patient between portable processing devices, comprising:
- a first portable processing device including,
  - a navigation processor supporting user navigation and selection of information to be transferred; and
  - a communication network for,
    - establishing a bidirectional communication link with a second portable processing device;
    - validating identification data of a medical information recipient associated with said second portable device to determine said recipient is authorized to access said selected information; and
    - communicating patient identification information and said selected information on said established communication link in response to user selection of a displayed icon.

* * * * *